United States Patent
Marshall et al.

(10) Patent No.: US 6,747,030 B1
(45) Date of Patent: Jun. 8, 2004

(54) PIPERAZINE DERIVATIVES AS 5-HT$_{1B}$ ANTAGONISTS

(75) Inventors: Howard Marshall, Harlow (GB); Mervyn Thompson, Harlow (GB); Paul Adrian Wyman, Harlow (GB)

(73) Assignee: SmithKline Beecham p.l.c. (GB)

( * ) Notice: Subject to any disclaimer, the term of this patent is extended or adjusted under 35 U.S.C. 154(b) by 0 days.

(21) Appl. No.: 10/089,013

(22) PCT Filed: Sep. 21, 2000

(86) PCT No.: PCT/EP00/09442
§ 371 (c)(1),
(2), (4) Date: Mar. 25, 2002

(87) PCT Pub. No.: WO01/23374
PCT Pub. Date: Apr. 5, 2001

(30) Foreign Application Priority Data

Sep. 25, 1999 (GB) .............................................. 9922831
Jan. 27, 2000 (GB) .............................................. 0001936
Jun. 7, 2000 (GB) .............................................. 0013873

(51) Int. Cl.$^7$ ..................... A61K 31/496; C07D 413/14
(52) U.S. Cl. ........................... 514/254.03; 514/253.09; 514/254.09; 514/252.11; 514/254.02; 514/254.05; 544/367; 544/364; 544/373; 544/357; 544/369; 544/366; 544/371
(58) Field of Search ................................ 544/367, 364, 544/373; 514/254.03, 253.09, 254.09

(56) References Cited

U.S. PATENT DOCUMENTS 5,696,122 A * 12/1997 Gaster et al. ................ 514/254
6,159,979 A * 12/2000 Gaster et al. .......... 514/252.12

FOREIGN PATENT DOCUMENTS

| EP | 0 533 268 | 3/1993 |
| WO | WO 95/06637 | 3/1995 |
| WO | WO 98/27058 | 6/1998 |
| WO | WO 98/47885 | 10/1998 |
| WO | WO 98/50358 | 11/1998 |
| WO | WO 99/29666 | 6/1999 |

OTHER PUBLICATIONS

Gaster et al., Annual Reports in Medicinal Chemistry vol. 33, pp. 21–30 (1998).*

* cited by examiner

*Primary Examiner*—Emily Bernhardt
(74) *Attorney, Agent, or Firm*—James M. Kanagy; Stephen Venetianer; Charles M. Kinzig

(57) ABSTRACT

Piperazine derivatives of formula(1),

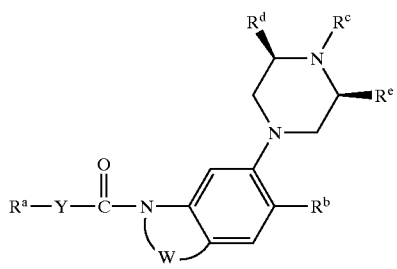

processes for their preparation, pharmaceutical compositions containing them in the treatment of CNS and other disorders and in their use in therapy as 5-HT$_{1B}$ antagonists are disclosed herein.

3 Claims, No Drawings

PIPERAZINE DERIVATIVES AS 5-HT$_{1B}$ ANTAGONISTS

This application is a Section 365(c) application based on PCT application serial number PCT/EP00/09442 filed Sep. 21, 2000 designating the US and claiming priority from GB 0013873.5, filed Jun. 7, 2000; GB 0001936.4, filed Jan. 27, 2000; and GB 9922831.4, filed Sep. 25, 1999.

The present invention relates to novel piperazine derivatives, processes for their preparation, pharmaceutical compositions containing the same and to their use in the treatment of CNS and other disorders.

WO 95/06637 discloses a series of piperazine derivatives which are said to possess 5-HT$_{1D}$ receptor antagonist activity. These compounds are alleged to be of use in the treatment of various CNS disorders such as depression. The human 5-HT$_{1D}$ receptor is now known to be encoded by two distinct genes initially designated 5-HT$_{1D\alpha}$ and 5-HT$_{1D\beta}$ and subsequently redesignated as 5-HT$_{1D}$ and 5-HT$_{1B}$ respectively (P. R. Hartig et al, Trends in Pharmacological Science, 1996, 17, 103–105). WO 98/50538 and WO 98/47885 disclose a series of piperazine derivatives that are said to exhibit combined 5-HT$_{1A}$, 5-HT$_{1B}$ and 5-HT$_{1D}$ receptor antagonist activity. WO 98/27058 discloses a series of carboxamide derivatives that are claimed to be 5-HT$_6$ receptor antagonists.

A structurally novel class of compounds has now been found which also exhibit 5-HT$_{1B}$ receptor activity. In a first aspect, the present invention therefore provides a compound of formula (I) or a pharmaceutically acceptable salt thereof:

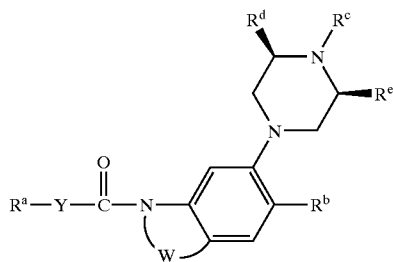

(I)

in which R$^a$ is a group of formula (i)

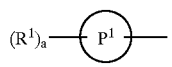

(i)

wherein P$^1$ is phenyl, naphthyl or heteroaryl;

R$^1$ is halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, nitro, CF$_3$, cyano, SR$^6$, SOR$^6$, SO$_2$R$^6$, SO$_2$R$^6$, SO$_2$NR$^6$R$^7$, CO$_2$R$^6$, CONR$^6$R$^7$, OCONR$^6$R$^7$, NR$^6$R$^7$, NR$^6$CO$_2$R$^7$, NR$^6$CONR$^7$R$^8$, CR$^6$=NOR$^7$ where R$^6$, R$^7$ and R$^8$ are independently hydrogen or C$_{1-6}$alkyl;

a is 0, 1, 2 or 3;

or R$^a$ is a group of formula (ii)

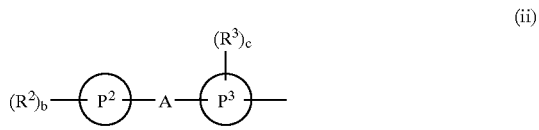

(ii)

wherein
P$^2$ is phenyl, naphthyl, heteroaryl or a 5 to 7 membered heterocyclic ring;
P$^3$ is phenyl, naphthyl or heteroaryl;
A is a bond or oxygen, carbonyl, CH$_2$ or NR$^4$ where R$^4$ is hydrogen or C$_{1-6}$alkyl;
R$^2$ is as defined above for R$^1$ in formula (i) or R$^2$ is heteroaryl optionally substituted by C$_{1-6}$alkyl, halogen or COC$_{1-6}$alkyl or is a 5–7 membered heterocyclic ring optionally substituted by oxo;
R$^3$ is halogen, C$_{1-6}$alkyl, C$_{3-6}$cycloalkyl, C$_{1-6}$alkoxy, COC$_{1-6}$alkyl, hydroxy, nitro, CF$_3$, cyano, CO$_2$R$^6$, CONR$^6$R$^7$, NR$^6$R$^7$ where R$^6$ and R$^7$ are as defined above;
b and c are independently 0, 1, 2 or 3;
Y is a single bond, CH$_2$, O or NR$^5$ where R$^5$ is hydrogen or C$_{1-6}$alkyl;
W is —(CR$^9$R$^{10}$)$_t$— where t is 2, 3 or 4 and R$^9$ and R$^{10}$ are independently hydrogen or C$_{1-6}$alkyl or W is a group CH=CH;
R$^b$ is hydrogen, halogen, hydroxy, C$_{1-6}$alkyl, CF$_3$, COC$_{1-6}$alkyl, cyano or C$_{1-6}$alkoxy;
R$^c$ is hydrogen or C$_{1-6}$alkyl;
R$^d$ and R$^e$ are independently C$_{1-4}$alkyl.

Alkyl groups, whether alone or as part of another group, may be straight chain or branched. The term 'halogen' is used herein to describe, unless otherwise stated, a group selected from fluorine, chlorine, bromine or iodine.

Where used herein the term naphthyl is intended, unless otherwise stated, to denote both naphth-1-yl and naphth-2-yl groups.

The term "heteroaryl" is intended to mean an aromatic or a benzofused aromatic ring containing 1 to 3 heteroatoms selected from oxygen, nitrogen and sulphur. Suitable examples of such aromatic rings include thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl and pyridyl. Suitable examples of such benzofused aromatic rings include quinolinyl, isoquinolinyl, indolyl, benzofuryl, benzothienyl, benzimidazolyl, benzoxazolyl and the like.

The term "5–7 membered heterocyclic ring" is used herein to mean a non aromatic ring containing 1 to 3 heteroatoms selected from oxygen, nitrogen and sulphur. Suitable examples of such non aromatic rings include piperidinyl, piperazinyl, pyrrolidinyl and morpholinyl.

The heteroaryl and 5–7 membered heterocyclic rings, as described above, may be linked to the remainder of the molecule via a carbon atom or, when present, a suitable nitrogen atom.

Within the Definition of R$^a$ Formula (i)

When P$^1$ is heteroaryl a preferred example is pyridyl. Preferably P$^1$ is phenyl or naphthyl, most preferably phenyl.

When a is other than 0, preferred R$^1$ groups include halogen (particularly fluoro or chloro), C$_{1-6}$alkyl group (particularly methyl), CF$_3$ and cyano. When a is 2 or 3 the groups R$^1$ can be the same or different.

Preferably a is 1 or 2, most preferably 2.

Within the Definition of $R^a$ Formula (ii)

Preferably A is a bond.

When $P^3$ is heteroaryl preferred examples include quinolinyl and pyrazolyl. $P^3$ is preferably phenyl or naphthyl. A preferred substitution arrangement for such naphthyl groups is 1,4 or 1,5, that is to say, a naphth-1-yl group in which the group A is attached at the 4 or 5 position respectively.

$P^2$ is preferably phenyl, a heteroaryl group such as pyridyl, pyrazinyl, oxadiazolyl or oxazolyl or $P^2$ is a 5–7 membered heterocycle such as piperidinyl.

When b is other than 0, preferred $R^2$ groups include halogen (particularly chloro), $C_{1-6}$alkyl group (particularly methyl), heteroaryl (particularly oxadiazolyl optionally substituted by $C_{1-6}$alkyl) or a 5–7 membered heterocyclic ring (particularly 2-oxo pyrrolidinyl). When b is 2 or 3 the groups $R^2$ may be the same or different. Preferably b is 0, 1 or 2.

When c is other than 0, preferred $R^3$ groups are halogen (particularly chloro) and $C_{1-6}$alkyl group (particularly methyl). When c is 2 or 3 the groups $R^3$ may be the same or different. Preferably c is 0 or 1.

A preferred group of formula (ii) is that in which A is a single bond, $P^2$ is pyridyl (particularly 2-pyridyl) and $P^3$ is naphthyl particularly naphth-1-yl). A further preferred group of formula (ii) is that in which A is a single bond, $P^2$ is pyridyl and $P^3$ is phenyl. Such groups may be optionally substituted by the preferred $R^2$ and $R^3$ groups as described above.

Y is preferably a single bond, $CH_2$ or a NH group.

It will be appreciated that when W is a group —CH=CH— an indole ring is formed. Within the definition of the group W, the groups $R^9$ and $R^{10}$ are each preferably hydrogen and t is preferably 2 or 3, most preferably 2.

$R^b$ is preferably hydrogen, $C_{1-6}$alkoxy group (particularly methoxy) or $C_{1-6}$alkyl group (particularly methyl).

$R^c$ is preferably hydrogen or methyl.

Preferably both $R^d$ and $R^e$ are methyl.

Preferred compounds of this invention are examples E1–E73 (as described below) or a pharmaceutically acceptable salt thereof. Particularly preferred compounds according to this invention are:

cis-1-[(2-chloro-3-trifluoromethylphenyl)acetyl]-6-(3,4,5-trimethylpiperazin-1-yl)indole, cis-1-[(2-fluoro-3-trifluoromethylphenyl)acetyl]-5-methoxy-6-(3,4,5-trimethylpiperazin-1-yl)indoline, cis-1-[(2,3dichlorophenyl)acetyl]-6-(3,5-dimethylpiperazin-1-yl)-5-methoxyindoline cis-6-(3,5-dimethylpiperazin-1-yl)-5-methoxy-1-[4-(2-methyl-6-(2-oxopyrrolidin-1-yl)pyridin-3-yl)benzoyl]indoline, cis-1-[(3-chloro-2-fluorophenyl)acetyl]-6-(3,5-dimethylpiperazin-1-yl)-5-methoxyindole, cis-1-[(2-fluoro-3-trifluoromethylphenyl)acetyl]-5-fluoro-6-(3,4,5-trimethylpiperazin-1-yl)indole, cis-1-[2-chloro-3-(trifluoromethyl)phenyl)aminocarbonyl]-5-methyl-6-(3,4,5-trimethylpiperazin-1-yl)indoline or a pharmaceutically acceptable salts thereof.

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1–19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid.

The compounds of formula (I) may be prepared in crystalline or non-crystalline form, and, if crystalline, may optionally be hydrated or solvated. This invention includes within its scope stoichiometric hydrates as well as compounds containing variable amounts of water.

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

Compounds of the invention can be prepared using procedures known in the art. In a further aspect the present invention also provides a process for the preparation of a compound of formula (I) or a pharmaceutically acceptable salt thereof which comprises either:

(a) where Y is NH, coupling a compound of formula (II):

$$R^a\text{—N=}(C\text{=}O) \qquad (II)$$

in which $R^a$ is as defined in formula (I) with a compound of formula (III):

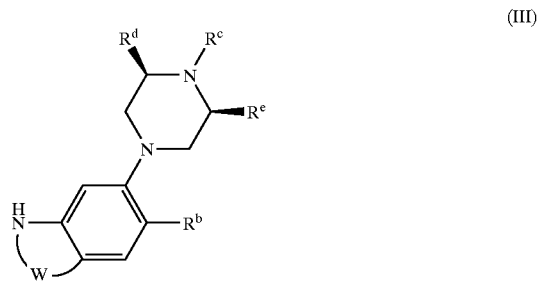

(III)

in which W, $R^b$, $R^c$, $R^d$ and $R^e$ are as defined in formula (I); or (b) where Y is $NR^5$, reacting a compound of formula (IV)

$$R^a\text{—}NR^5H \qquad (IV)$$

in which $R^a$ and $R^5$ are as defined in formula (I) with a compound of formula (III) as defined above together with an appropriate urea forming agent; or (c) where Y is a single bond, $CH_2$ or O, reacting a compound of formula (V)

$$R^a\text{—Y—}(C\text{=}O)\text{—L} \qquad (V)$$

in which $R^a$ is as defined in formula (I) and L is an appropriate leaving group, with a compound of formula (III) as defined above; and optionally thereafter for either process (a), (b) or (c):

removing any protecting groups, converting a compound of formula (I) into another compound of formula (I), forming a pharmaceutically acceptable salt.

The reaction in process (a) is conveniently effected in an organic solvent such as dichloromethane.

In process (b) the urea forming agent can be carbonyl diimidazole, triphosgene or phosgene, and carried out in an inert organic solvent such as dimethylformamide, tetrahydrofuran or dichloromethane at ambient or elevated temperature in the presence of a base such as triethylamine or pyridine.

In process (c) the leaving group L may be a halogen e.g. chloro group and the reaction may be carried out in an inert organic solvent such as tetrahydrofuran or dichloromethane at ambient or elevated temperature in the presence of a base such as triethylamine or pyridine. Alternatively L may be an O-benzotriazole group, prepared from hydroxybenzotriazole and a carbodiimide, and the reaction may be carried out in an inert organic solvent such as tetrahydrofuran, dichloromethane or dimethylformamide at ambient or elevated temperature.

Compounds of formula (I) can be converted into further compounds of formula (I) using standard techniques. The following examples are given by way of illustration of this point rather than limitation. For compounds of formula (I) wherein $R^c$ is hydrogen, it is possible to introduce a $C_{1-6}$alkyl group by conventional alkylation using 1 molar equivalent of a $C_{1-6}$alkyl halide and 1 molar equivalent of a suitable base in an inert solvent. For compounds of formula (I) wherein W is a group —$CH_2CH_2$—, it is possible to convert this to a group wherein W is —CH=CH— with an oxidising agent such as 2,3-dichloro-5,6-dicyano-1,4-benzoquinone in an inert solvent such as dichloromethane or toluene.

Intermediate compounds of formula (II), (III), (IV) and (V) are either commercially available or can be prepared using methods described herein, by methods known to those skilled in the art or by analogous methods thereto. For example, where intermediates of formula (V) are derived from phenylacetic acids, the latter may be prepared from the corresponding benzoic acids by standard homologation methods involving reduction to the benzyl alcohol, followed by conversion to the benzyl bromide, displacement with an inorganic cyanide to afford the benzonitrile, followed by acid or base hydrolysis.

It will be appreciated to those skilled in the art that it may be necessary to protect certain reactive substituents during some of the above procedures. Standard protection and deprotection techniques can be used. For example, primary amines can be protected as phthalimide, benzyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art.

Pharmaceutically acceptable salts may be prepared conventionally by reaction with the appropriate acid or acid derivative.

The involvement of serotonin (5-hydroxytryptamine; 5-HT) receptors in a number of pharmacological effects has been reviewed by R. A. Glennon in "Serotonin Receptors: Clinical Implications", Neuroscience and Behavioural Reviews, 1990, 14, 35 and by L. O. Wilkinson and C. T. Dourish in "Serotonin Receptor Subtypes: Basic and Clinical Aspects" S. Peroutka Ed., John Wiley and Sons, New York, 1991 p. 147.

Serotonin receptors have been implicated in pharmacological effects such as mood disorders including depression, seasonal affective disorder and dysthymia, anxiety disorders, including generalized anxiety, panic disorder, agoraphobia, social phobia, obsessive compulsive disorder and post-traumatic stress disorder, memory disorders, including dementia, amnesic disorders and age-associated memory impairment; disorders of eating behaviours, including anorexia nervosa and bulimia nervosa, sleep disorders (including disturbances of circadian rhythm), motor disorders such as Parkinson's disease, dementia in Parkinson's disease, neuroleptic-induced Parkinsonism and tardive dyskinesias, pain disorders as well as other psychiatric disorders such as schizophrenia and psychosis. Serotonin receptor ligands have been shown to be of use in the treatment of emesis and nausea and may also be of use in endocrine disorders such as hyperlactinaemia, vasospasm (particularly in the cerebral vasculature), cerebellar ataxia and hypertension, as well as disorders of the gastrointestinal tract where changes in motility and secretion are involved. They may also be of use in the treatment of pre-menstrual tension, sexual dysfunction and hypothermia.

Ligands with high affinity for the 5-$HT_1$ receptors are well recognised as having therapeutic utility for the treatment of the above conditions. It has been suggested that a selective 5-$HT_{1B}$ receptor antagonist should act as a fast onset antidepressant (P. Blier Trends Pharmacol. Sci. 1994, 15, 220).

The present invention also provides for a compound of formula (I) or a pharmaceutically acceptable salt for use in the treatment of the aforementioned disorders. In particular, the invention provides for a compound of formula (I) or a pharmaceutically acceptable salt for use in the treatment or prophylaxis of depression.

In a further aspect the invention provides a method of treating disorders where an antagonist of the 5-$HT_{1B}$ receptor is beneficial, particularly the aforementioned disorders, which comprises administering a safe and therapeutically effective amount of compound of formula (I) or a pharmaceutically acceptable salt to a patient in need thereof.

In another aspect, the invention provides the use of a compound of formula (I) or a pharmaceutically acceptable salt thereof in the manufacture of a medicament for the treatment or prophylaxis of disorders in which an antagonist of the 5-$HT_{1B}$ receptor is beneficial, particularly the aforementioned disorders, more particularly depression.

The affinities of the compounds of this invention for the 5-$HT_{1B}$ receptor can be determined by the following radioligand binding assay. CHO cells expressing 5-$HT_{1B}$ receptors ($4 \times 10^7$ cells/ml) are homogenised in Tris buffer $Mg^{2+}$ and stored in 1.0 ml aliquots. 0.4 ml of a cell suspension is incubated with [$^3$H]-5-HT (4 nM) in Tris Mg HCl buffer (pH 7.7) and test drug, at 37° C. for 45 minutes. Each test drug is tested at 10 concentrations (0.01 mM to 0.3 nM final concentration), with non-specific binding defined using 0.01 mM 5-HT. The total assay volume is 0.5 ml. Incubation is stopped by rapid filtration using a Tomtec Harvester (filters pre-washed in 0.3% polyethylenimine) and radioactivity measured by Topcount scintillation counting. pKi values are calculated from the $IC_{50}$ generated by an iterative least squares curve fitting programme.

All examples tested in accordance with this radioligand binding assay were found to have a pKi>7.3 at 5-$HT_{1B}$ receptors with many demonstrating a pKi in the higher range of 8.0–9.2.

The selectivity of the compounds of this invention for 5-$HT_{1B}$ receptors can be determined using binding assay methods which are well known to those skilled in the art. All examples tested were found to have a greater than a 10-fold selectivity over 5-$HT_{1D}$ receptors and a greater than 50-fold selectivity over other binding sites within the CNS, in particular, other 5-HT receptor sub-types and dopaminergic receptors. Many examples were found to have a greater than a 30fold selectivity over 5-$HT_{1D}$ receptors and a greater than 80-fold selectivity over other binding sites.

The intrinsic activity of the compounds of this invention can be determined according to the following procedure.

CHO cell membranes stably expressing human 5-HT$_{1B}$ receptors are homogenised in HEPES/EDTA buffer and stored in 1 ml aliquots, and [$^{35}$S]GTPγS binding studies are carried out essentially as described by Lazareno et al., (Life Sci., 1993, 52, 449) with some minor modifications. Membranes from 10$^6$ cells are pre-incubated at 30° C. for 30 minutes in 20 mM HEPES buffer (pH 7.4) in the presence of MgCl$_2$ (3 mM), NaCl (100 mM), GDP (10 µM) and ascorbate (0.2 mM), with or without compounds. The reaction is started by the addition of 50 µl of [$^{35}$S]GTPγS (100 pm, assay concentration) followed by a further 30 minutes incubation at 30° C. Non-specific binding was determined using non-radiolabelled GTPγS (20 µM) added prior to the membranes. The reaction is terminated by rapid filtration through Whatman GF/B grade filters followed by 5×1 ml washes with ice cold HEPES (20 mM)/MgCl$_2$ (3 mM) buffer. Radioactivity is measured using liquid scintillation spectrometry. This procedure is hereafter referred to as the [$^{35}$S]GTPγS functional assay.

It has been found, using the [$^{35}$S]GTPγS functional assay, that certain compounds of formula (I) show varying levels of intrinsic efficacy, which is defined by a scale in which the value 1.0 defines the maximum response elicited by the agonist 5-HT, 0.0 defines antagonism and a negative value indicates inverse agonism. The difficulties in describing intrinsic activity of drugs acting at G protein coupled receptors is recognised in the art (Hoyer and Boddeke, Trends in Pharmacological Sciences, July 1993, [Vol. 14], page 270–275). We believe that however these ligands are classified according to this functional assay, the compounds of this invention will be useful antidepressants in vivo. It is believed that the preferred compounds of this invention will display 5-HT$_{1B}$ antagonist activity in vivo and that such compounds will have a rapid onset of action. A rapid onset of action is particularly advantageous for antidepressant compounds: by 'rapid onset of action' we mean that a therapeutic response is seen within 7 days from first administration of the compound, as opposed to a period of about 21 days or more which is typical of SSRI's, tricyclic antidepressants and buspirone.

Compounds of formula (I) which have an intrinsic activity of 0.5 or less in the in vitro [$^{35}$S]GTPγS functional assay are preferred, as these compounds are more likely to be full antagonists in vivo. Particularly preferred compounds of this invention have an intrinsic activity in the range 0.0–0.3 or are inverse agonists in this functional assay.

It has been found that the compounds of this invention have a particularly advantageous profile in that they demonstrate high affinity and selectivity for the 5-HT$_{1B}$ receptor together with low intrinsic activity in the [$^{35}$S]GTPγS functional assay.

It will be appreciated by those skilled in the art that the compounds according to the invention may advantageously be used in conjunction with one or more other therapeutic agents, for instance, different antidepressant agents.

In order to use the compounds of formula (I) in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three times a day. Such therapy may extend for a number of weeks or months.

All publications, including but not limited to patents and patent applications, cited in this specification are herein incorporated by reference as if each individual publication were specifically and individually indicated to be incorporated by reference herein as though fully set forth.

The following descriptions and Examples illustrate the preparation of compounds of the invention.

Description 1

1-Acetyl-6-bromo-5-methoxyindoline (D1)

A stirred solution of 1-acetyl-6-bromoindolin-5-ol (Tetrahedron 1973, 29(8), 1115; 40 g, 0.15 mole) in DMF (500 ml) was treated with K$_2$CO$_3$ (61 g, 0.45 mole) and iodomethane (11.7 ml, 0.19 mole) and maintained at room temperature for 20 h, then concentrated under vacuum to 200 ml. The residue was treated with water (200 ml) and the precipitate filtered off, dried and recrystallised from EtOAc to afford the title compound as a white solid (35.7 g, 85%).

Description 2 cis-1-Acetyl-5-methoxy-6-(3,4,5-trimethylpiperazin-1-yl)indoline (D2)

A mixture of palladium (II) acetate (500 mg), 2,2'-bis(diphenylphosphino)-1,1'-binaphthyl (2.0 g) and cesium carbonate (10.3 g) in dry degassed 1,4-dioxane (120 ml) under argon was sonicated at 28° C. for 0.5 h producing a pink heterogeneous mixture. This was treated with D1 (6.0 g, 22 mmole) followed by cis-1,2,6-trimethylpiperazine (J. Med. Chem. 1968, 11, 592; 4.8 g, 38 mmole) and heated with rapid stirring at reflux for 70 h. The mixture was allowed to cool, filtered, then concentrated under vacuum. The residue was treated with water and extracted with EtOAc. The organic solution was then extracted with 1M HCl acid and the aqueous extract was basified by addition of $K_2CO_3$ and extracted with EtOAc. The extract was dried ($Na_2SO_4$) and concentrated under vacuum to leave an orange solid, which was chromatographed on silica gel eluting with 0–10% MeOH/DCM to afford the required product as a pale yellow solid (1.6 g, 23%).

Description 3 cis-5-Methoxy-6-(3,4,5-trimethylpiperazin-1-yl)indoline (D3)

A stirred solution of D2 (1.6 g, 5 mmole) in 2M HCl acid (50 ml) was heated under reflux for 2 h, then the solution was allowed to cool, basified with $K_2CO_3$ and extracted with DCM. The extract was dried ($Na_2SO_4$) and concentrated under vacuum to afford the title compound as a pale orange solid (1.4 g, 100%).

Description 4 cis-1-Acetyl-6-(4-benzyl-3,5-dimethylpiperazin-1-yl)-5-methoxyindoline (D4)

The title compound was prepared in 43% yield from cis-1-benzyl-2,6-dimethylpiperazine (Org. Prep. Proc. 1976, 8, 19) and D1 using a similar procedure to Description 2.

Description 5 cis-6-(4-Benzyl-3,5-dimethylpiperazin-1-yl)-5-methoxyindoline (D5)

The title compound was prepared from D4 by a similar procedure to Description 3 as a beige solid (100%)

Description 6 cis-6-(4-Benzyl-3,5-dimethylpiperazin-1-yl)-5-methoxy-1-[4-(6-methylpyridin-2-yl)-1-naphthoyl]indoline (D6)

The title compound was prepared from D5 and D13 following a similar procedure to Example 1 as a white solid (85%).

Description 7

Methyl 4-(trimethylstannyl)-1-naphthoate (D7)

A stirred solution of methyl 4bromo-1-naphthoate (Collect. Czech. Chem. Commun. 1997, 62(11), 1737; 7.3 g, 28 mmole) in degassed toluene (300 ml) was treated with hexamethylditin (10 g, 31 mmole) and tetrakis(triphenylphosphine)palladium(0) (720 mg) and heated at reflux under argon for 3 h. On cooling, the mixture was filtered through Celite (Diatomaceous Earth), concentrated under vacuum and the residue chromatographed on silica gel eluting with 0–3% ether/60–80 petrol to afford the title compound as a colourless oil (9.06 g, 94%).

Description 8

Methyl 4-(pyridin-4-yl)-1-naphthoate (D8)

A stirred solution of D7 (9.06 g, 26 mmole) in dry degassed DMF (150 ml) was treated with copper (I) iodide (495 mg, 2.6 mmole), dichlorobis(triphenylphosphine)palladium(II) (1.52 g, 2.2 mmole) and 4-bromopyridine (prepared by suspending the HCl salt (6.07 g, 31 mmole) in 40% KOH solution, extracting with toluene and adding the dried toluene solution to the reaction). The mixture was heated at reflux under argon for 5 h and allowed to cool before removing the DMF under vacuum. The residue was partitioned between EtOAc and 10% $NaHCO_3$ solution and the organics dried ($Na_2SO_4$) and chromatographed on silica gel eluting with EtOAc to afford the title compound as a white solid (4.1 g, 60%).

Description 9

Methyl 4-(1-methylpiperidin-4-yl)-1-naphthoate (D9)

A stirred solution of D8 (2.0 g, 7.6 mmole) in acetone (20 ml) was treated with methyl iodide (1.0 ml, 15 mmole), stirred for 0.5 h and then allowed to stand at room temperature for 2 days. The resultant yellow precipitate was filtered off to afford the pyridinium salt as yellow crystals (2.87 g). This was dissolved in EtOH (30 ml) and DMF (90 ml) and was hydrogenated at 50 psi (344.8 KPa) and room temp over $PtO_2$ for 24 h. The mixture was filtered through Celite (Diatomaceous Earth) and the filtrate concentrated under vacuum to a brown oil. This was partitioned between DCM and 10% $NaHCO_3$ solution and the organic solution separated, dried ($Na_2SO_4$) and concentrated under vacuum to afford the title compound as a brown oil (1.82 g, 91%).

Description 10

Methyl 4-(piperidin-4-yl)-1-naphthoate (D10)

A solution of D9 (0.39 g, 1.4 mmole) in DCM (30 ml) was treated with $iPr_2EtN$ (0.26 g, 2 mmole) followed by 1-chloroethyl chloroformate (0.29 g, 2 mmole) and stirred at room temperature for 3 h, then concentrated under vacuum and the residue treated with MeOH (30 ml) and heated under reflux for 1 h. The mixture was allowed to cool and the solid filtered off, washed with $Et_2O$ and dried. This was treated with 10% $Na_2CO_3$ solution, extracted with DCM and the extract dried and concentrated under vacuum to afford the title compound as a colourless oil (0.33 g, 88%).

Description 11

4-(1-tert-Butoxycarbonylpiperidin-4-yl)-1-naphthoic acid (D11)

A solution of D10 (0.33 g, 1.2 mmole) in DCM (30 ml) was treated with di-tert-butyl dicarbonate (0.28 g, 1.25 mmole) and stirred at room temperature for 20 h, then concentrated under vacuum to leave a white solid (0.44 g). This was dissolved in THF (15 ml) and MeOH (15 ml), treated with LiOH (85 mg) in water (10 ml) and stirred at room temperature for 20 h, then concentrated under vacuum to approx. 10 ml. The residue was treated with excess 10% aqueous citric acid and extracted with EtOAc. The extract was dried and concentrated under vacuum to afford the title compound as a white solid (0.41 g, 97%).

Description 12 cis-1-[4-(1-tert-Butoxycarbonylpiperidin-4-yl)-1-naphthoyl]-5methoxy-6-(3,4,5-trimethylpiperazin-1-yl)indoline (D12)

The title compound was prepared from D11 and D3 using a similar procedure to Example 8 as a pink solid (52%).

Description 13

4-(6-Methylpyridin-2-yl)-1-naphthoic acid (D13)

The title compound was prepared from D7 and 2-bromo-6-methylpyridine using a similar method to Description 8 (45%), followed by hydrolysis of the methyl ester using 1M NaOH solution (69%) to afford a white solid.

Description 14

Methyl 4-(trimethylstannyl)1-naphthylacetate (D14)

The title compound was prepared from methyl 4-bromo-1-naphthylacetate (Zh. Org. Khim. 1966, 2, 1852) using a similar procedure to Description 7 as a colourless oil (69%).

Description 15

4-(6-Methylpyridin-2-yl)-1-naphthylacetic acid (D15)

The title compound was prepared from D14 and 2-bromo-6-methylpyridine using a similar method to Description 8 (32%), followed by hydrolysis of the methyl ester using 1M NaOH solution (80%) to afford a white solid.

Description 16

4-Formyl-1-naphthylboronic acid (D16)

A mixture of K10 montmorillonite clay (75 g) and trimethylorthoformate (75 ml) in methanol (75 ml) was stirred at room temperature for 0.5 h, then filtered. The solid was added to a stirred solution of 4-bromo-1-naphthylcarboxaldehyde (JP 01113354 [1989], 25.70 g, 0.11 mole) in DCM (300 ml). After 18 h the mixture was filtered, washed with 20% $K_2CO_3$ solution (100 ml), dried and concentrated in vacuo to afford the dimethyl acetal as a yellow oil (29.05 g 95%), which was dissolved in anhydrous THF (300 ml) at −70° C. and treated with a 1.6M solution of n-butyllithium in THF (78 ml, 0.12 mole). After 1 h triisopropyl borate (24.4 g, 0.13 mole) was added over 0.25 h, the mixture stirred for 1 h at −70° C. then poured into 2M HCl (500 ml). The mixture was concentrated to 50% volume in vacuo, and extra ted with EtOAc. The organic solution was then extracted with 10% NaOH solution (4×50 ml) and the combined aqueous solution acidified with 6M HCl and extracted with DCM (3×100 ml). The extract was dried and concentrated to dryness in vacuo to afford the title compound as a yellow-green powder (13.15 g, 64%).

Description 17

4-Carboxy-1-naphthylboronic acid (D17)

To a stirred solution of D16 (0.25 g, 1.25 mmole) and NaOH (0.15 g, 3.75 mmole) in water (5 ml) at 0° C. was added dropwise a solution of $KMnO_4$ (0.19 g. 0.120 mmole) in water (5 ml). After 0.25 h sodium metabisulphite (excess) was added and the mixture acidified with 6M HCl and extracted with EtOAc (3×15 ml). The extracts were dried and concentrated to dryness to afford the title compound as cream powder (0.21 g, 78%).

Description 18

4-(2,6-Dimethylpyridin-3-yl)-1-naphthoic acid (D18)

A stirred mixture of D17 (0.32 g, 1.5 mmole), 3-bromo-2,6-dimethylpyridine hydrochloride (Synthesis 1974, 4, 293; 0.37 g, 1.6 mmole), $Na_2CO_3$ (0.48 g, 5.6 mmole) and tetrakis(triphenylphosphine)palladium (0) (0.08 g, 0.07 mmole) in 50% DME/water (20 ml) was heated at reflux under argon for 18 h. The mixture was concentrated in vacuo to 50% volume, diluted with water (20 ml), washed with EtOAc (2×10 ml), acidified with 2M HCl to pH 4 and extracted with DCM (3×25 ml). The combined extract was dried and evaporated to dryness. The residue was triturated in $Et_2O$ to afford the title compound as a buff powder (0.29 g, 69%).

Description 19

4-(3,6-Dimethylpyrazin-2-yl)-1-naphthoic acid (D19)

The title compound was prepared from D17 and 2-chloro-3,6-dimethylpyrazine using a similar procedure to Description 18 as a cream powder (50%).

Description 20

4-(1-Methyl-6-oxo-1,6-dihydropyridin-3-yl)-1-naphthoic acid (D20)

The title compound was prepared from 3-bromo-1-methyl-6-oxo-1,6-dihydropyridine (Khim.Geterotsikl. soedin. 1982, 12, 1662) and D17 using a similar procedure to Description 18 as a buff powder (78%).

Description 21 cis-7-(4-Benzyl-3,5-dimethylpiperazin-1-yl)-6-methoxyquinoline (D21)

The title compound was prepared from cis-1-benzyl-2,6-dimethylpiperazine (Org. Prep. Proc. 1976, 8, 19) and 7-bromo-6-methoxyquinoline (J. Org. Chem. 1990, 55, 2019) using a similar procedure to Description 2 (75%).

Description 22 cis-7-(3,5-Dimethylpiperazin-1-yl)-6-methoxy-1,2,3,4-tetrahydroquinoline (D22)

A solution of D21 (6.8 g, 19 mmole) in EtOH (200 ml) and THF (200 ml) was hydrogenated over 10% Pd-C (1 g) at ambient temperature and pressure for 48 h, then filtered through Kieselguhr and the filtrate hydrogenated over Pt (1.5 g of $PtO_2$) at ambient temperature and 50 psi (344.8 Kpa) for 20 h. The mixture was filtered through Kieselguhr and the filtrate concentrated under vacuum to afford the title compound as a colourless oil (3.3 g, 63%).

Description 23 cis-1-Acetyl-7-(3,5-dimethylpiperazin-1-yl) methoxy-1,2,3,4-tetrahydroquinoline (D23)

A stirred solution of D22 (2.4 g, 8.7 mmole) in DCM (100 ml) at 0° C. was treated with acetic anhydride (0.92 g, 9

Description 24 cis-1-Acetyl-6-methoxy-1,2,3,4-tetrahydro-7-(3,4,5-trimethylpiperazin-1-yl)quinoline (D24)

A stirred solution of D23 (2.7 g, 8.5 mmole) in MeOH (60 ml) at room temperature under Ar was treated with aqueous formaldehyde (3.2 ml of 37% w/v, 40 mmole), followed by portionwise addition of NaBH$_3$CN (1.1 g, 17 mmole). The pH of the mixture was adjusted to 6 by addition of formic acid and stirred at room temperature for 6 h, then concentrated under vacuum and the residue treated with 10% Na$_2$CO$_3$ solution and extracted with DCM. The extract was dried, concentrated under vacuum and the residue chromatographed on silica gel eluting with 0–20% MeOH/EtOAc to afford the title compound as a yellow solid (1.4 g, 50%).

Description 25 cis-6-Methoxy-1,2,3,4-tetrahydro-7-(3,4,5-trimethylpiperazin-1-yl)quinoline (D25)

The title compound was prepared from D24 using a similar procedure to Description 3 as a yellow solid (86%).

Description 26 cis-1-Acetyl-6-(4-benzyl-3,5-dimethylpiperazin-1-yl)indoline (D26)

The title compound was prepared from cis-1-benzyl-2,6-dimethylpiperazine (Org. Prep. Proc. 1976, 8, 19) and 1-acetyl-6-bromoindoline (Heterocycles 1987, 26, 2817) using a similar procedure to Description 2 as an off-white solid (53%).

Description 27 cis-1-Acetyl-6-(3,4,5-trimethylpiperazin-1-yl)indoline (D27)

The title compound was prepared from D26 by hydrogenation over 10% Pd-C using a similar procedure to Example 45, followed by N-methylation using a similar procedure to Description 24 to afford a white solid (59%).

Description 28 cis-6-(3,4,5-trimethylpiperazin-1-yl)indoline (D28)

The title compound was prepared from D27 using a similar procedure to Description 3 to afford an off-white solid (96%).

Description 29 cis-1-Acetyl-5-chloro-6-(3,4,5-trimethylpiperazin-1-yl)indoline (D29)

A solution of D27 (1.0 g, 3.5 mmole) in DCM (20 ml) under argon was treated with N-chlorosuccinimide (929 mg, 7.0 mmole) and stirred at room temp. for 3 h. The mixture was washed with water, dried and evaporated under vacuum to a buff solid. Column chromatography on silica gel eluting with 5% MeOH/DCM afforded the title compound as a white solid (670 mg, 60%).

Description 30 cis-5-Chloro-6-(3,4,5-trimethylpiperazin-1-yl)indoline (D30)

The title compound was prepared from D29 using a similar procedure to Description 3 to afford an off-white solid (72%).

Description 31 cis-1-Acetyl-5bromo-6-(3,4,5-trimethylpiperazin-1-yl)indoline (D31)

A solution of D27 (884 mg, 3.1 mmole) in DCM (15 ml) at 0° C. under argon was treated with N-bromosuccinimide (819 mg, 4.6 mmole) and stirred at room temp. for 2 days. Additional NBS was added (150 mg, 0.84 mmole) and stirring continued for 16 h. The mixture was washed with 10% Na$_2$CO$_3$ solution, dried and concentrated under vacuum. The residue was purified by column chromatography on silica gel eluting with 5% MeOH/DCM to afford the title compound as a beige solid (440 mg, 39%).

Description 32 cis-5-Bromo-6-(3,4,5-trimethylpiperazin-1-yl)indoline (D32)

A solution of D28 (250 mg, 1.0 mmole) in DCM (40 ml) under argon was treated with trifluoroacetic anhydride (0.15 ml, 1.1 mmole) and stirred at room temp for 2 h. Evaporation in vacuo afforded a yellow oil (100%) which was re-dissolved in DCM (10 ml) and treated immediately with N-bromosuccinimide (356 mg, 2.0 mmole). The mixture was stirred under argon at room temp. for 16 h, washed with water, dried and evaporated in vacuo to afford a yellow solid (100%), which was dissolved in MeOH (30 ml) and treated under argon with Na$_2$CO$_3$ (500 mg, 4.7 mmole) then stirred at room temperature for 2 days. The mixture was evaporated in vacuo and partitioned between water and DCM. The organics were dried and evaporated to afford the title compound as a beige solid (264 mg, 80%).

Description 33 cis-1-Acetyl-5-ethyl-6-(3,4,5-trimethylpiperazin-1-yl)indoline (D33)

A stirred suspension of D31 (200 mg, 0.55 mmole) in dry DMF (5 ml) was treated with tributyl(vinyl)tin (0.24 ml, 0.83 mmole) and the mixture degassed by bubbling argon through for 40 minutes. To the mixture was added Et$_3$N (0.15 ml, 1.1 mmole) and tetrakis(triphenylphosphine) palladium (0) (64 mg, 0.06 mmole) and the mixture heated under argon at reflux for 18 h. On cooling, the mixture was diluted with EtOAc (100 ml) and extracted with 0.5M HCl (2×). The aqueous was basified (K$_2$CO$_3$), extracted with DCM, dried and evaporated to a buff solid, which was dissolved in EtOH (10 ml) and hydrogenated over 10% Pd/C (20 mg) at room temp. and atmospheric pressure for 2 days. Filtration through Celite (Diatomaceous Earth) and evaporation in vacuo afforded the title compound as a buff solid (100 mg, 62%).

Description 34 cis-5-Ethyl-6-(3,4,5-trimethylpiperazin-1-yl)indoline (D34)

The title compound was prepared from D33 using a similar procedure to Description 3 to afford a buff solid (84%).

Description 35 cis-6-(3,5-Dimethylpiperazin-1-yl)-5-methoxyindoline (D35)

The title compound was prepared from D4 by hydrogenation over 10% Pd/C using a similar procedure to Example 45 (98%), followed by hydrolysis in 2M HCl using a similar procedure to Description 3 (80%) to afford the product as a pale brown solid

Description 36 cis-1-Acetyl-5-methyl-6-(3,4,5-trimethylpiperazin-1-yl)indoline (D36)

The title compound was prepared from D31 and tetramethyltin using a similar procedure to Description 33 (20%).

Description 37 cis-5-Methyl-6-(3,4,5-trimethylpiperazin-1-yl)indoline (D37)

The title compound was prepared from D36 using a similar procedure to Description 3 (86%).

Description 38 cis-5-Fluoro-6-(3,4,5-trimethylpiperazin-1-yl)indoline (D38)

The title compound was prepared from 1-acetyl-6-bromo-5-fluoroindoline (prepared by bromination of 5-fluoroindoline analogous to procedure in J. Het. Chem. 1983, 20, 349, followed by N-acylation) by reaction with cis-3,5-dimethylpiperazine using similar procedure to Description 2 (82%), followed by N-methylation using procedure similar to Description 24 (69%), followed by hydrolysis as in Description 3 (96%). The product was isolated as a pale yellow solid.

Description 39

N-(4-Acetyl-2-bromophenyl)-N-(2-methylallyl)acetamide (D39)

N-(4-Acetyl-2-bromophenyl)acetamide (25 g, 0.1 mole) in dry DMF (250 ml) was treated with sodium hydride (60%, 4.5 g, 0.11 mole) at 25° C. under argon with stirring for 1 h. 3-Bromo-2-methylpropene (1.1 ml, 0.11 mole) was added and the mixture stirred for a further 16 h. The mixture was concentrated in vacuo and partitioned between water and $Et_2O$. The organic phase was dried and concentrated in vacuo to give the title compound (32.8 g, 100%).

Description 40

1-(5-Acetyl-3,3-dimethylindolin-1-yl)ethanone (D40)

D39 (32.8 g, 0.1 mole) in toluene (3L) was stirred at 80° C. under argon and a solution of tri-n-butyltin hydride (40 ml) and AIBN (0.9 g) in toluene (250 ml) added over 25 minutes The mixture was heated at reflux for 4 h and concentrated in vacuo. The whole was partitioned between EtOAc and aq.$K_2CO_3$ and the organic phase gave a residue which on trituration with ether gave the title compound as a solid (10.7 g, 46%).

Description 41

5-Acetoxy-1-acetyl-3,3-dimethylindoline (D41)

D40 (10.7, 0.05 mole) in glacial AcOH (60 ml) was stirred at 25° C. under argon and a solution of peracetic acid (30%, 22 ml, 0.09 mole) in AcOH (10 ml) added over 30 minutes The mixture was kept at 25° C. for 20 h, diluted with water (250 ml) and extracted with DCM. The organic phase was washed (water, aq.metabisulfite, aq.$K_2CO_3$) dried ($Na_2SO_4$) and concentrated to afford the title compound (10.2 g, 91%).

Description 42

1-(3,3-Dimethyl-5-hydroxyindolin-1-yl)ethanone (D42)

D41 (10.2, 0.04 mole) in MeOH (100 ml) and 2M NaOH (52 ml) was stirred at 25° C. under argon for 4 h. Acidification with conc. $H_2SO_4$ gave a solid which was collected by filtration, washed with water and dried in vacuo to give D42 (7.8 g, 92%).

Description 43

1-(3,3-Dimethyl-5-methoxyindolin-1-yl)ethanone (D43)

D42 (7.8, 0.04 mole) in DMF (100 ml) was treated with methyl iodide (4.73 ml, 0.08 mole), $K_2CO_3$ (11.1 g, 0.08 mole) and stirred at 25° C. under argon for 24 h. The mixture was diluted with water (500 ml) and extracted exhaustively with $Et_2O$ and concentrated to afford the title compound (6.4 g, 77%).

Description 44

1-(6-Bromo-3,3-dimethyl-5-methoxyindolin-1-yl)ethanone (D44)

D43 (6.4, 0.03 mole) in 2:1DCM:MeOH (420 ml) was stirred at 25° C. under argon; benzyltrimethylammonium tribromide (13.3 g, 0.34 mole) was added portionwise and stirring continued for 5 h. The mixture was evaporated to dryness and work-up with DCM/aq.$K_2CO_3$ afforded the title compound (8.7 g, 100%).

Description 45 cis-1-Acetyl-3,3-dimethyl-6-(3,5-dimethylpiperazin-1-yl)-5-methoxyindoline (D45)

A mixture of palladium (II) acetate (650 mg), 2,2'-bis (diphenylphosphino)-1,1'-binaphthyl (2.7 g) and cesium carbonate (13.5 g) in dry degassed 1,4-dioxane (200 ml) under argon was sonicated at 28° C. for 0.5 h. This was treated with cis-2,6-dimethylpiperazine (4.6 g, 0.04 mole) and D44 (7.4 g, 0.025 mole) using a method similar to that of Description 2 to give the title compound as a solid (1.6 g, 19%).

Description 46 cis-3,3-Dimethyl-5-methoxy-6-(3,4,5-trimethylpiperazin-1-yl)indoline (D46)

D45 was treated with aqueous formaldehyde and sodium cyanoborohydride followed by acid hydrolysis using a procedure similar to that of Descriptions 24 and 3 to give the title compound as a waxy solid. $MH^+304$.

Description 47

4-(2,5-Dimethylpyridin-4-yl)benzoic acid

The title compound was prepared from 4-bromo-2,5-dimethylpyridine (WO 93/15062) and 4-carboxyphenylboronic acid using a similar procedure to Description 18 as a white solid (67%).

Description 48 cis-1,5-Diacetyl-6-(3,4,5-trimethylpiperazin-1-yl)indoline

A solution of D31 (0.75 g, 2.0 mmole) and (1-ethoxyvinyl)tributyltin (1.08 g, 3.0 mmole) in dry DMF was treated with tetrakis(triphenylphosphine)palladium(0) (0.12 g, 0.10 mmole) and triethylamine (0.56 ml, 4.0 mmole). The mixture was heated to 100° C. under argon for 16 h. The cooled mixture was diluted with EtOAc (120 ml), extracted with 2M HCl (3×30 ml) and the extracts were basified with $K_2CO_3$ and extracted with DCM (4×30 ml). The extracts were dried ($Na_2SO_4$), concentrated to dryness in vacuum and the residue was chromatographed on silica gel eluting with 5% MeOH/DCM to afford the crude title compound as a brown oil (0.45 g, 67%).

Description 49 cis-5-Acetyl-6-(3,4,5-trimethylpiperazin-1-yl)indoline

A solution of D48 (0.44 g, 1.34 mmole) in EtOH (5 ml) and 2M HCl (5 ml) was stirred at room temperature for 5 days. It was then concentrated under vacuum, diluted with water (20 ml), basified with $K_2CO_3$ and extracted with DCM (3×15 ml). The extracts were dried ($Na_2SO_4$) and concentrated under vacuum. The residue was chromatographed on silica gel eluting with 0–10% MeOH/DCM to afford the title compound as a brown gum (0.21 g, 55%).

EXAMPLE 1 cis-5-Methoxy-1-[4-(6-methylpyridin-2-yl)-1-naphthoyl]-6-(3,4,5-trimethylpiperazin-1-yl)indoline (E1)

A suspension of D13 (92 mg, 0.35 mmole) in DCM (10 ml) was treated with oxalyl chloride (75 mg, 0.60 mmole) and stirred at room temperature for 18 h, then concentrated under vacuum to leave the acid chloride as a yellow solid. This was re-dissolved in DCM (10 ml) and added to a stirred solution of D3 (100 mg, 0.38 mmole) and pyridine (47 mg, 0.60 mmole) in DCM (10 ml) at 0° C. under argon. The reaction mixture was allowed to warm to room temperature and stir for 3 h, then treated with polystyrene bound methylisocyanate (100 mg of 1.2 mmole/g) and stirred for 18 h, then filtered through Kieselguhr. The filtrate was washed with 10% $Na_2CO_3$ solution, dried ($Na_2SO_4$), concentrated under vacuum and the residue purified by chromatography on basic alumina eluting with EtOAc to afford the title compound as a yellow solid (110 mg, 60%).

$^1$H NMR (250 MHz, $CDCl_3$)—spectrum highly complex due to hindered rotation with most peaks doubled up. Major peaks discernible: δ6.75 & 6.68 (2×s, together 1H=4<u>H</u>), 3.87 & 3.75 (2×s, together 3H=O<u>Me</u>), 3.16 & 3.00 (2×t, together 2H,=indoline C<u>H</u>$_2$), 2.69 (s, 3H,=pyridyl <u>Me</u>), 2.34 & 2.12 (2×s, together 3H,=piperazine N-<u>Me</u>), 1.17 & 0.85 & 0.79 (3×d, together 6H,=3 and 5-piperazine <u>Me</u>). MH$^+$521.

Examples E2–E8 were prepared by a similar method to that of Example 1 using D3 or D25 and an appropriate acid chloride derivative consistent with the final product:

| Example | MH$^+$ |
|---|---|
| cis-5-Methoxy-1-[5-(6-methylpyridin-2-yl)-1-naphthoyl]-6-(3,4,5-trimethylpiperazin-1-yl)indoline (E2) | 521 |
| cis-5-Methoxy-1-[5-(2-methyloxazol-5-yl)-1-naphthoyl]-6-(3,4,5-trimethylpiperazin-1-yl)indoline (E3) | 511 |
| cis-1-(2,3-Dichlorobenzoyl)-5-methoxy-6-(3,4,5-trimethylpiperazin-1-yl)indoline (E4) | 448/450 |
| cis-5-Methoxy-1-[2'-methyl-4'-(5-methyl-1,2,4-oxadiazol-3-yl)biphenyl-4-carbonyl]-6-(3,4,5-trimethylpiperazin-1-yl)indoline (E5) (acid ref: EP 0533268A1) | 552 |
| cis-5-Methoxy-1-[(3-nitrophenyl)acetyl]-6-(3,4,5-trimethylpiperazin-1-yl)indoline (E6) | 439 |
| cis-6-Methoxy-1-[4-(6-methylpyridin-2-yl)-1-naphthoyl]-1,2,3,4-tetrahydro-7-(3,4,5-trimethylpiperazin-1-yl)quinoline (E7) | 535 |

EXAMPLE 8 cis-1-[(2-Chloro-3-trifluoromethylphenyl)acetyl]-6-(3,4,5-trimethylpiperazin-1-yl)indoline (E8)

A solution of 2-chloro-3-trifluoromethylphenylacetic acid (954 mg, 4.0 mmole) and D28 (950 mg, 3.87 mmole) in DCM (100 ml) was treated with 1-[3-(dimethylamino)propyl]-3-ethylcarbodiimide hydrochloride (766 mg, 4.0 mmole) and 1-hydroxybenzotriazole hydrate (612 mg, 4.0 mmole) and stirred at room temp. for 0.5 h. The reaction mixture was washed with 10% $Na_2CO_3$ solution, dried ($Na_2SO_4$) and concentrated under vacuum to afford the title compound as a pale yellow solid (1.15 g, 64%).

$^1$H NMR (250 MHz, $CDCl_3$) δ7.94 (d, 1H), 7.67 (d, 1H), 7.56 (d, 1H), 7.38 (t, 1H), 7.07 (d, 1H), 6.60 (dd, 1H), 4.19 (t, 2H), 3.98 (s, 2H), 3.45 (br d, 2H), 3.17 (m, 2H), 2.53 (t, 2H), 2.34 (m, 2H), 2.22 (s, 3H), 1.13 (d, 6H). MH$^+$466/468.

EXAMPLE 9 cis-1-[(2-Fluoro-3-trifluoromethylphenyl)acetyl]-5-methoxy-6-(3,4,5-trimethylpiperazin-1-yl)indoline (E9)

The title compound was prepared from 2-fluoro-3-trifluoromethylphenylacetic acid (155 mg, 0.70 mmole) and D3 (150 mg, 0.54 mmole) using a similar procedure to Example 8. The product was obtained as a pale yellow oil (210 mg, 81%), which was converted to its hydrochloride salt as a beige solid.

$^1$H NMR (free base) (250 MHz, $CDCl_3$) δ7.91 (s, 1H), 7.65–7.50 (m, 2H), 7.25 (t, 1H), 6.72 (s, 1H), 4.17 (t, 2H), 3.84 (s, 3H & s, 2H), 3.35–3.25 (m, 2H), 3.19 (t,2H), 2.55–2.40 (m, 4H), 2.30 (s, 3H), 1.11 (d, 6H). MH$^+$480.

Examples E10–E43 were prepared by a similar method to that of Example 8 using the appropriate indoline (D3, D28, D30, D32, D34, D35, D37 or D38) and the appropriate carboxylic acid consistent with the final product:

| Example | MH$^+$ |
|---|---|
| cis-1-[(2,3-Dichlorophenyl)acetyl]-6-(3,5-dimethylpiperazin-1-yl)-5-methoxyindoline (E10) | 448/450 |
| cis-1-[(3-Chloro-2-fluorophenyl)acetyl]-6-(3,4,5-trimethylpiperazin-1-yl)indoline (E11) | 416/418 |
| cis-1-[(2,3-Difluorophenyl)acetyl]-6-(3,4,5-trimethylpiperazin-1-yl)indoline (E12) | 400 |
| cis-1-[(2,3-Dichlorophenyl)acetyl]-6-(3,4,5-trimethylpiperazin- | 432/434 |

-continued

| Example | MH+ |
|---|---|
| 1-yl)indoline (E13) | |
| cis-1-[(2-Trifluoromethylphenyl)acetyl]-6-(3,4,5-trimethylpiperazin-1-yl)indoline (E14) | 432 |
| cis-1-[(2,3-Dichlorophenyl)acetyl]-5-methoxy-6-(3,4,5-trimethylpiperazin-1-yl)indoline (E15) | 462/464 |
| cis-1-[(2-Trifluoromethylphenyl)acetyl]-5-methoxy-6-(3,4,5-trimethylpiperazin-1-yl)indoline (E16) | 462 |
| cis-1-[(3-Chloro-2-fluorophenyl)acetyl]-5-methoxy-6-(3,4,5-trimethylpiperazin-1-yl)indoline (E17) | 446/448 |
| cis-1-[(2,3-Difluorophenyl)acetyl]-5-methoxy-6-(3,4,5-trimethylpiperazin-1-yl)indoline (E18) | 430 |
| cis-5-Methoxy-1-[4-(6-methylpyridin-2-yl)-1-naphthylacetyl]-6-(3,4,5-trimethylpiperazin-1-yl)indoline (E19) | 535 |
| cis-5-Chloro-1-[4-(6-methylpyridin-2-yl)-1-naphthoyl]-6-(3,4,5-trimethylpiperazin-1-yl)indoline (E20) | 525/527 |
| cis-1-[4-(2,6-Dimethylpyridin-3-yl)-1-naphthoyl]-5-methoxy-6-(3,4,5-trimethylpiperazin-1-yl)indoline (E21) from D18 | 535 |
| cis-1-[4-(3,6-Dimethylpyrazin-2-yl)-1-naphthoyl]-5-methoxy-6-(3,4,5-trimethylpiperazin-1-yl)indoline (E22) from D19 | 536 |
| cis-5-Methoxy-1-[4-(1-methyl-6-oxo-1,6-dihydropyridin-3-yl)-1-naphthoyl]-6-(3,4,5-trimethylpiperazin-1-yl)indoline (E23) (from D20) | 536 |
| cis-1-[(2-Fluoro-3-trifluoromethylphenyl)acetyl]-5-methyl-6-(3,4,5-trimethylpiperazin-1-yl)indoline (E24) | 464 |
| cis-1-[(2-Chloro-3-fluorophenyl)acetyl]-5-methoxy-6-(3,4,5-trimethylpiperazin-1-yl)indoline (E25) | 446/448 |
| cis-1-[(2-Bromo-3-fluorophenyl)acetyl]-5-methoxy-6-(3,4,5-trimethylpiperazin-1-yl)indoline (E26) | 490/492 |
| cis-1-[(2-Bromo-3-chlorophenyl)acetyl]-5-methoxy-6-(3,4,5-trimethylpiperazin-1-yl)indoline (E27) | 508/509 |
| cis-1-[(2-Fluoro-3-trifluoromethylphenyl)acetyl]-6-(3,5-dimethylpiperazin-1-yl)-5-methoxyindoline (E28) | 466 |
| cis-1-[(2-Chloro-3-trifluoromethylphenyl)acetyl]-6-(3,5-dimethylpiperazin-1-yl)-5-methoxyindoline (E29) | 482/484 |
| cis-1-[(3-Chloro-2-fluorophenyl)acetyl]-6-(3,5-dimethylpiperazin-1-yl)-5-methoxyindoline (E30) | 432/434 |
| cis-1-[(2-Chloro-3-trifluoromethylphenyl)acetyl]-5-methoxy-6-(3,4,5-trimethylpiperazin-1-yl)indoline (E31) | 496/498 |
| cis-1-[(2-Fluoro-3-trifluoromethylphenyl)acetyl]-5-fluoro-6-(3,4,5-trimethylpiperazin-1-yl)indoline (E32) | 468 |
| cis-1-[(3-Fluoro-2-trifluoromethylphenyl)acetyl]-5-methoxy-6-(3,4,5-trimethylpiperazin-1-yl)indoline (E33) | 480 |
| cis-1-[(3-Chloro-2-cyanophenyl)acetyl]-5-methoxy-6-(3,4,5-trimethylpiperazin-1-yl)indoline (E34) | 453/455 |
| cis-1-[(2-Acetyl-3-chlorophenyl)acetyl]-5-methoxy-6-(3,4,5-trimethylpiperazin-1-yl)indoline (E35) | 470/472 |
| cis-1-[(3-Bromo-2-methylphenyl)acetyl]-5-methoxy-6-(3,4,5-trimethylpiperazin-1-yl)indoline (E36) | 486/488 |
| cis-1-[(3-Cyano-2-methylphenyl)acetyl]-5-methoxy-6-(3,4,5-trimethylpiperazin-1-yl)indoline (E37) | 433 |
| cis-5-Bromo-1-[(2-chloro-3-trifluoromethylphenyl)acetyl]-6-(3,4,5-trimethylpiperazin-1-yl)indoline (E38) | 545/546 |
| cis-5-Acetyl-1-[(2-chloro-3-trifluoromethylphenyl)acetyl]-6-(3,4,5-trimethylpiperazin-1-yl)indoline (E39) | 508/510 |
| cis-5-Methoxy-1-[2-phenyl-3-(trifluoromethyl)pyrazol-4-ylcarbonyl]-6-(3,4,5-trimethylpiperazin-1-yl)indoline (E40) | 514 |
| cis-6-(3,5-Dimethylpiperazin-1-yl)-1-[(4-(2,5-dimethylpyridin-4-yl)benzoyl]-5-methoxyindoline (E41) (from acid D47) | |
| cis-6-(3,5-Dimethylpiperazin-1-yl)-5-methoxy-1-[2'-methyl-4'-(2-oxopyrrolidin-1-yl)biphenyl-4-carbonyl]indoline (E42) (acid ref: Description 47 in WO 97/34901) | 539 |
| cis-6-(3,5-Dimethylpiperazin-1-yl)-5-methoxy-1-[2'-methyl-4'-(5-methyl-1,2,4-oxadiazol-3-yl)biphenyl-4-carbonyl]indoline (E43) (acid ref: EP0533268A1) | 538 |

EXAMPLE 44 cis-6-(3,5-Dimethylpiperazin-1-yl)-5-methoxy-1-[4-(2-methyl-6-(2-oxopyrrolidin-1-yl)pyridin-3-yl)benzoyl]-indoline (E44)

Methyl [4-(2-methyl-6-(2-oxopyrrolidin-1-yl)pyridin-3-yl)benzoate (Description 9 in WO 97/17351) was hydrolysed with 2M NaOH solution to afford the corresponding carboxylic acid, which was coupled with D35 using a similar procedure to Example 8 to afford the title compound. Hydrochloride salt obtained as an off-white solid.

$^1$H NMR (250 MHz, CDCl$_3$) δ [rotamers—key signals quoted] 8.00 (br, 1H, indoline), 7.59 & 8.27 (Abq, 2H, J=8 Hz, pyridyl), 7.40 & 7.62 (Abq, 4H, J=8 Hz, phenyl), 6.75 (s, 1H, indoline), 3.85 (s, 3H, OMe), 3.10 (t, 2H, J=8 Hz), 2.68 (t, 2H, J=8 Hz), 2.47 (s, 3H, pyrMe), 2.14 (m, 2H), 1.13 (br, 6H). MH+540.

EXAMPLE 45 cis-6-(3,5-Dimethylpiperazin-1-yl)-5-methoxy-1-[4-(6-methylpyridin-2-yl)-1-naphthoyl]indoline (E45)

A solution of D6 (380 mg, 0.64 mmole) in EtOH (50 ml) and THF (50 ml) was treated with 10% Pd-C (300 mg) and stirred under a hydrogen atmosphere at ambient temperature and pressure for 70 h. The mixture was filtered through Kieselguhr and concentrated under vacuum. The residue was purified by chromatography on basic alumina eluting with EtOAc followed by crystallisation from Et$_2$O to afford the title compound as a yellow solid (320 mg, 98%). MH+507.

EXAMPLE 46 cis-1-[(2-Chloro-3-trifluoromethylphenyl)acetyl]-5-cyano-6-(3,4,5-trimethylpiperazin-1-yl)indoline (E46)

A stirred mixture of E38 (67 mg, 0.12 mmole) and copper cyanide (43 mg, 0.48 mmole) in DMF (2 ml) was heated to 130° C. for 16 h. The cooled mixture was added to conc. aqueous ammonia (50 ml), stirred for 30 mins., then extracted with DCM (3×25 ml). The extracts were dried Na$_2$SO$_4$) and concentrated to dryness in vacuum. The residue was dissolved in DCM (2 ml) and applied to an SCX resin cartridge (1 g) and the resin eluted with DCM (×2), MeOH (×3) and the washings discarded. Final elution with 1M NH$_3$ in MeOH (×2) afforded the title compound as a pale brown powder (26 mg, 43%). MH+491/493.

EXAMPLE 47 cis-1-[(3-Aminocarbonyl-2-methylphenyl)acetyl]-5-methoxy-6-(3,4,5-trimethylpiperazin-1-yl)indoline (E47)

To a stirred suspension of E37 (80 mg, 0.19 mmole) and K$_2$CO$_3$ (26 mg, 0.19 mmole) in DMSO (1 ml) was added dropwise 30% aq. H$_2$O$_2$ soln.(0.1 ml), then the mixture was warmed to 100° C. for 2 mins. and allowed to cool to room temperature. After 30 mins a further 0.1 ml of 30% aq. H$_2$O$_2$ soln. was added and the mixture again warmed to 100° C. for 2 mins. and allowed to cool. This procedure was repeated twice more, and then the mixture was stirred at room temperature for 16 h. It was diluted with water (50 ml) and extracted with DCM (3×20 ml), the extracts dried (Na$_2$SO$_4$) and concentrated to dryness under vacuum. The residue was triturated in Et$_2$O to afford the title compound as a cream powder (52 mg, 63%). MH+451.

EXAMPLE 48 cis-5-Methoxy-1-[4-(1-methylpiperidin-4-yl)-1-naphthoyl]-6-(3,4,5-trimethylpiperazin-1-yl)indoline (E48)

A stirred solution of D3 (58 mg, 0.21 mmole) in toluene (5 ml) under argon was treated with 2M trimethylaluminium in toluene (0.13 ml, 0.25 mmole), then stirred at room temperature for 0.75 h. A solution of D9 (60 mg, 0.21 mmole) in toluene (5 ml) was added and the mixture was heated under reflux for 3.5 h, then allowed to cool to room temperature. The mixture was added to a 5 g silica gel column and eluted with 0–10% MeOH/DCM to afford a yellow oil. This was further purified by preparative plate TLC on silica gel eluting with 9:1:0.1 DCM/MeOH/0.88 NH$_3$ to afford the title compound as a white solid (39 mg, 35%). MH$^+$ 527.

EXAMPLE 49 cis-5-Methoxy-1-[4-(piperidin-4-yl)-1-naphthoyl]-6-(3,4,5-trimethylpiperazin-1-yl)indoline (E49)

A solution of D12 (45 mg, 0.074 mmole) in DCM (10 ml) was treated with trifluoroacetic acid (3 ml) and stirred at room temperature for 3 h, then concentrated under vacuum. The residue was dissolved in DCM and washed with 10% Na$_2$CO$_3$ solution, dried and concentrated under vacuum. The residue was purified by silica gel chromatography followed by trituration with Et$_2$O to afford the title compound as a pale brown solid (23 mg, 61%). MH$^+$ 513.

EXAMPLE 50 cis-1-[(2-Chloro-3-trifluoromethylphenyl)acetyl]-6-(3,4,5-trimethylpiperazin-1-yl)indole (E50)

A solution of E8 (1.8 g, 3.86 mmole) in DCM (150 ml) was treated with a solution of 2,3-dichloro-5,6-dicyano-1,4-benzoquinone (908 mg, 4.0 mmole) in DCM (50 ml) and the mixture stirred at room temp. under argon for 20 mins. The mixture was washed with 10% Na$_2$CO$_3$ solution, dried (Na$_2$SO$_4$), and evaporated to a brown oil. Column chromatography on silica gel (eluent 5% MeOH/DCM) afforded the title compound as a yellow semi-solid (1.1 g, 61%), which was converted to its hydrochloride salt as a white solid.

$^1$H NMR (free base) (250 MHz, CDCl$_3$) δ8.06 (d, 1H), 7.72 (dd, 1H), 7.55 (d, 1H), 7.42 (m, 3H), 6.98 (dd, 1H), 6.61 (d, 1H), 4.45 (s, 2H), 3.49 (m, 2H), 2.59 (t, 2H), 2.40 (m, 2H), 2.31 (s, 3H), 1.15 (d, 6H). MH$^+$ 464/466.

Examples E51–E56 were prepared by a similar method to that of Example 50.

| Example | MH$^+$ |
|---|---|
| cis-1-[(2-Fluoro-3-trifluoromethylphenyl)acetyl]-5-methoxy-6-(3,4,5-trimethylpiperazin-1-yl)indole (E51) | 478 |
| cis-1-(2,3-Dichlorophenylaminocarbonyl)-5-methoxy-6-(3,4,5-trimethylpiperazin-1-yl)indole (E52) (from E60) | 461 |
| cis-5-Methoxy-1-[4-(6-methylpyridin-2-yl)-1-naphthyl-acetyl]-6-(3,4,5-trimethylpiperazin-1-yl)indole (E53) (from E19) | 533 |
| cis-1-[(3-Chloro-2-fluorophenyl)acetyl]-6-(3,5-dimethylpiperazin-1-yl)-5-methoxyindole (E54) (from E30) | 430/432 |
| cis-1-[(2,3-Dichlorophenyl)acetyl]-6-(3,5-dimethyl-piperazin-1-yl)-5-methoxyindole (E55) (from E10) | 446/448/449 |
| cis-1-[(2-Fluoro-3-trifluoromethylphenyl)acetyl]-5-fluoro-6-(3,4,5-trimethylpiperazin-1-yl)indole (E56) (from E32) | 466 |

EXAMPLE 57 cis-5-Methoxy-1-[4-(6-methylpyridin-2-yl)-1-naphthylaminocarbonyl]-6-(3,4,5-trimethylpiperazin-1-yl)indoline (E57)

A stirred mixture of D13 (87 mg, 0.33 mmole), triethylamine (40 mg, 0.40 mmole) and diphenylphosphoryl azide (96 mg, 0.35 mmole) in toluene was heated at reflux under argon for 0.5 h, then allowed to cool to room temperature and treated with a solution of D3 (70 mg, 0.25 mmole) in DCM (10 ml). The mixture was stirred at room temperature for 4 h, then treated with polystyrene bound trisamine (80 mg of 3.6 mmole/g) and polystyrene bound methylisocyanate (60 mg of 1.2 mmole/g) and stirred at room temperature for 70 h, then filtered through Kieselguhr. The filtrate was washed with 10% Na$_2$CO$_3$ solution, dried (Na$_2$SO$_4$), concentrated under vacuum and purified by chromatography on basic alumina eluting with EtOAc, followed by trituration with Et$_2$O to afford the title compound as a yellow solid (70 mg, 52%).

$^1$H NMR (250 MHz, CDCl$_3$) δ8.13 (d, 1H), 7.98 (d, 1H), 7.90 (d, 1H), 7.78–7.70 (m, 2H), 7.61 (d, 1H), 7.60–7.45 (m, 2H), 7.34 (d, 1H), 7.21 (d, 1H), 6.76 (s, 1H), 6.75 (s, 1H), 4.25 (t, 2H), 3.85 (s, 3H), 3.38–3.21 (m, 4H), 2.67 (s, 3H), 2.55–2.40 (m, 4H), 2.30 (s, 3H), 1.09 (d, 6H). MH$^+$ 536.

Examples E58–E65 were prepared by a similar method to that of Example 57 from indoline D3 or D37 and the appropriate carboxylic acid consistent with the final product:

| Example | MH$^+$ |
|---|---|
| cis-5-Methoxy-1-[5-(6-methylpyridin-2-yl)-1-naphthylaminocarbonyl]-6-(3,4,5-trimethylpiperazin-1-yl)indoline (E58) | 536 |
| cis-5-Methoxy-1-[5-(2-methyloxazol-5-yl)-1-naphthylaminocarbonyl]-6-(3,4,5-trimethylpiperazin-1-yl)indoline (E59) | 526 |
| cis-1-(2,3-Dichlorophenylaminocarbonyl)-5-methoxy-6-(3,4,5-trimethylpiperazin-1-yl)indoline (E60) | 463/465 |
| cis-1-(3-Chloro-2-fluorophenylaminocarbonyl)-5-methoxy-6-(3,4,5-trimethylpiperazin-1-yl)indoline (E61) | 447/449 |
| cis-1-[3-Fluoro-2-(trifluoromethyl)phenylaminocarbonyl]-5-methoxy-6-(3,4,5-trimethylpiperazin-1-yl)indoline (E62) | 481 |
| cis-1-[2-Chloro-3-(trifluoromethyl)phenylaminocarbonyl]-5-methoxy-6-(3,4,5-trimethylpiperazin-1-yl)indoline (E63) | 497/499 |
| cis-1-[2-Chloro-3-methylphenyl)amiocarbonyl]-5-methoxy-6-(3,4,5-trimethylpiperazin-1-yl)indoline (E64) | 443/445 |
| cis-1-[2-Chloro-3-(trifluoromethyl)phenyl)aminocarbonyl]-5-methyl-6-(3,4,5-trimethylpiperazin-1-yl)indoline (E65) | 481/483 |

EXAMPLE 66 cis-1-(2,3-Dichlorophenylaminocarbonyl)-6-(3,4,5-trimethylpiperazin-1-yl)indoline (E66)

A solution of D28 (10 mg, 0.04 mmole) in DCM (1 ml) was treated with 2,3-dichlorophenyl isocyanate (10 mg, 0.05 mmole) and stirred at room temp for 16 h. The mixture was applied to an SCX resin cartridge (500 mg) and the resin eluted with DCM (×2), MeOH (×3) and the washings discarded. Final elution with 1M NH$_3$ in MeOH (×2) afforded the title compound as an off white solid (12 mg, 69%). MH$^+$ 433/435.

Examples E67–E72 were prepared by a similar method to that of Example 66 using indoline (D3, D30, D32 or D34) and the appropriate phenyl isocyanate consistent with the final product.

| Example | MH$^+$ |
|---|---|
| cis-1-(2,3-Dichlorophenylaminocarbonyl)-5-chloro-6-(3,4,5-trimethylpiperazin-1-yl)indoline (E67) | 467/469 |
| cis-1-(2,3-Dichlorophenylaminocarbonyl)-5-bromo-6-(3,4,5- | 513/515 |

-continued

| Example | MH+ |
|---|---|
| trimethylpiperazin-1-yl)indoline (E68) | |
| cis-1-(2,3-Dichlorophenylaminocarbonyl)-5-ethyl-6-(3,4,5-trimethylpiperazin-1-yl)indoline (E69) | 461/463 |
| cis-5-Methoxy-1-[2-(trifluoromethyl)phenylaminocarbonyl]-6-(3,4,5-trimethylpiperazin-1-yl)indoline (E70) | 433 |
| cis-1-[2-Fluoro-3-(trifluoromethyl)phenylaminocarbonyl]-5-methoxy-6-(3,4,5-trimethylpiperazin-1-yl)indoline (E71) | 480 |
| cis-1-[2-Chloro-3-(trifluoromethyl)phenylaminocarbonyl]-3,3-dimethyl-5-methoxy-6-(3,4,5-trimethylpiperazin-1-yl)indoline (E72) | 525 |

EXAMPLE 73 cis-1-[(2-Chloro-3-trifluoromethyl)phenoxycarbonyl]-5-methoxy-6-(3,4,5-trimethylpiperazin-1-yl)indoline (E73)

Triphosgene (40 mg, 0.13 mmole) was added to a stirred solution of D3 (100 mg, 0.36 mmole) in DCM (10 ml) which was maintained at room temperature for 1 h, then treated with 2-chloro-3-(trifluoromethyl)phenol (78 mg, 0.40 mmole) and triethylamine (0.062 ml, 0.44 mmole). The mixture was heated under reflux for 4 h, additional phenol (78 mg) and triethylamine (0.062 ml) added and heating continued for a further 8 h. The mixture was washed with 10% $K_2CO_3$ solution, dried and concentrated under vacuum. The title compound was purified by chromatography on silica gel (84 mg, 47%). MH+ 498/500.

What is claimed is:

1. A compound which is cis-6-(3,5-dimethylpiperazin-1-yl)-5-methoxy-1-[2'-methyl-4'-(5-methyl-1,2,4-oxadiazol-3-yl)biphenyl-4-carbonyl]indoline, its hydrochloride salt, or another pharmaceutically acceptable salt thereof.

2. A pharmaceutical composition comprising a pharmaceutically carrier or excipient and the compound of claim 1 and/or a pharmaceutically acceptable salt thereof.

3. A method for treating depression which comprises administering to a mammal in need thereof an effective amount of the compound of claim 1 and/or a pharmaceutically acceptable salt thereof, alone or in combination with a pharmaceutically acceptable carrier or excipient.

* * * * *